(12) United States Patent
Pflanz et al.

(10) Patent No.: US 9,790,462 B2
(45) Date of Patent: Oct. 17, 2017

(54) DEVICE AND METHOD FOR TREATING A FILTRATION MEDIUM

(71) Applicant: Sartorius Stedim Biotech GmbH, Goettingen (DE)

(72) Inventors: Karl Pflanz, Gleichen (DE); Alexandra Scholz, Goettingen (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 136 days.

(21) Appl. No.: 14/418,638

(22) PCT Filed: Jun. 10, 2013

(86) PCT No.: PCT/EP2013/001691
§ 371 (c)(1),
(2) Date: Jan. 30, 2015

(87) PCT Pub. No.: WO2014/019634
PCT Pub. Date: Feb. 6, 2014

(65) Prior Publication Data
US 2016/0017274 A1    Jan. 21, 2016

(30) Foreign Application Priority Data
Jul. 31, 2012   (DE) .................. 10 2012 015 063

(51) Int. Cl.
*G01N 1/00* (2006.01)
*B01L 3/00* (2006.01)
(Continued)

(52) U.S. Cl.
CPC ............ *C12M 47/06* (2013.01); *C12M 47/02* (2013.01); *C12N 1/02* (2013.01); *C12Q 1/6806* (2013.01)

(58) Field of Classification Search
CPC ............... B01L 3/5635; B01L 3/50255; B01L 2300/0681; G01N 1/4077;
(Continued)

(56) References Cited

U.S. PATENT DOCUMENTS 5,234,585 A * 8/1993 Zuk, Jr. ................. B01D 29/05
                                                              210/188
5,264,184 A * 11/1993 Aysta .................... B01D 61/18
                                                              210/473
(Continued)

FOREIGN PATENT DOCUMENTS

DE          10054632          3/2002
EP          2402456           1/2012
(Continued)

OTHER PUBLICATIONS

Translation International Preliminary Report on Patentability and Written Opinion.
(Continued)

*Primary Examiner* — Brian R Gordon
(74) *Attorney, Agent, or Firm* — Gerald E. Hespos; Michael J. Porco; Matthew T. Hespos

(57) ABSTRACT

A device (1) and a method are provided for treating a porous filtration medium (37) having a receiving unit (2) with of a receiving part (5) and a base part (6). The porous filtration medium (37) can be lifted by the receiving part (5) from a lower part (33) of a filtration device (32), and the receiving part (5) with the porous filtration medium (37) can be mounted on the base part (6). The receiving part (5) is latchable to the base part (6). The base part (6), towards the filtration medium (37) has an incubation chamber (17) connected to a base part (6) outlet (3) that faces away from the receiving part (5), and the outlet (3) has a projection onto which a receiving vessel (4) containing a solvent (28) for
(Continued)

dissolving the porous filtration medium (37) can be detachably pushed on.

8 Claims, 8 Drawing Sheets

(51) Int. Cl.
  *B01D 35/16* (2006.01)
  *C12M 1/00* (2006.01)
  *C12N 1/02* (2006.01)
  *C12Q 1/68* (2006.01)

(58) Field of Classification Search
  CPC .......... G01N 2001/4008; C12M 47/02; C12M 47/06; C12C 1/6806; C12N 1/02
  See application file for complete search history.

(56) References Cited

U.S. PATENT DOCUMENTS

| | | | | |
|---|---|---|---|---|
| 5,374,401 | A * | 12/1994 | von Berg | A61B 5/15003 422/534 |
| 5,849,249 | A * | 12/1998 | Jones, Jr. | B01D 11/0219 210/406 |
| 5,968,246 | A * | 10/1999 | Pomrink | C09D 1/00 106/14.14 |
| 6,269,957 | B1 * | 8/2001 | Bowers | B01D 61/18 210/321.6 |
| 6,405,876 | B1 * | 6/2002 | Seshimoto | B01D 61/18 210/488 |
| 6,632,681 | B1 * | 10/2003 | Chu | A61B 10/0045 422/502 |
| 6,761,855 | B1 * | 7/2004 | Cook | G01N 30/6052 210/198.2 |
| 7,434,483 | B2 * | 10/2008 | Cueni | B01L 3/0275 422/534 |
| 7,798,333 | B2 * | 9/2010 | Zuk, Jr. | B01D 29/085 210/406 |
| 8,414,778 | B2 * | 4/2013 | Tajima | B01D 61/145 210/103 |
| 8,580,560 | B1 * | 11/2013 | Ellis | B01D 15/165 210/232 |
| 8,697,436 | B2 | 4/2014 | Pflanz et al. | |
| 8,808,552 | B2 * | 8/2014 | Lin | B01D 29/085 210/232 |
| 9,182,326 | B2 * | 11/2015 | Kurowski | B01L 3/502715 |
| 2004/0072375 | A1 * | 4/2004 | Gjerde | B01J 20/285 436/541 |
| 2005/0232820 | A1 * | 10/2005 | Reed | G01N 35/028 422/552 |
| 2006/0273003 | A1 * | 12/2006 | Sudo | B01D 63/081 210/498 |
| 2010/0028933 | A1 | 2/2010 | Pflanz | |
| 2011/0243816 | A1 * | 10/2011 | Shimada | A61B 10/0038 422/547 |
| 2011/0293490 | A1 * | 12/2011 | Gjerde | B01J 20/291 422/535 |
| 2012/0248022 | A1 | 10/2012 | Pflanz | |
| 2012/0297899 | A1 * | 11/2012 | Scott | G01N 30/14 73/863.23 |
| 2013/0157277 | A1 | 6/2013 | Hacker et al. | |
| 2016/0074860 | A1 * | 3/2016 | Mitsuhashi | B04B 3/00 436/63 |
| 2016/0184743 | A1 * | 6/2016 | Marshall | B01L 3/0275 210/767 |
| 2016/0216177 | A1 * | 7/2016 | Rivat | G01N 1/4077 |
| 2016/0317748 | A1 * | 11/2016 | Seymour | A61M 5/165 |

FOREIGN PATENT DOCUMENTS

| | | |
|---|---|---|
| JP | 2012019723 | 2/2012 |
| WO | 0222866 | 3/2002 |

OTHER PUBLICATIONS

L. J. DiMichele (Am. Soc. Brew. Chem., 1993, vol. 51, No. 2, pp. 63-66).

K. Nakamura (Journal of Aerosol Research, 2003, vol. 18, No. 3, pp. 177-180).

K. Staerk (Applied and Environmental Microbiology, 1998, vol. 64, No. 2, pp. 543-548).

K. Sen (Applied and Environmental Microbiology, 2007, vol. 73, No. 22, pp. 7380-7387).

* cited by examiner

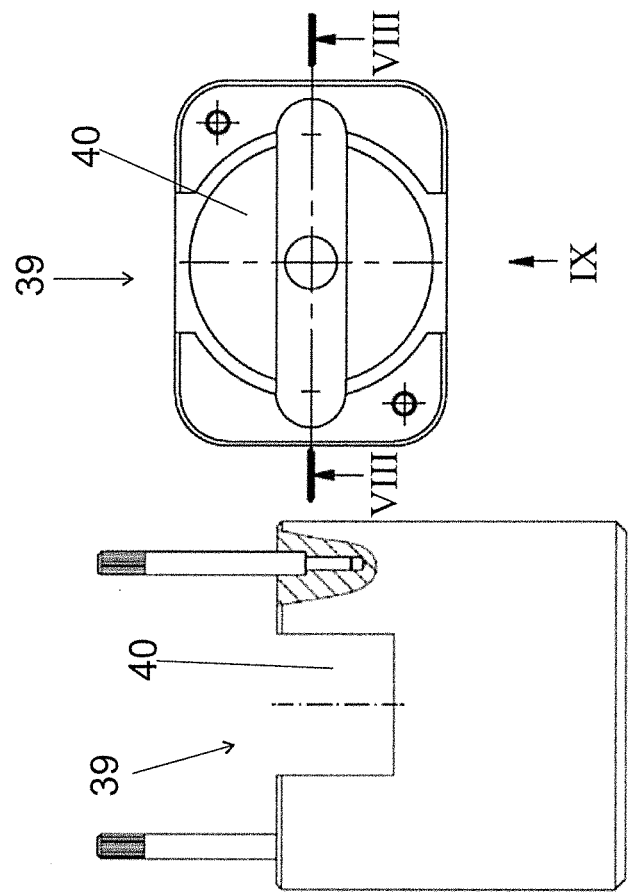
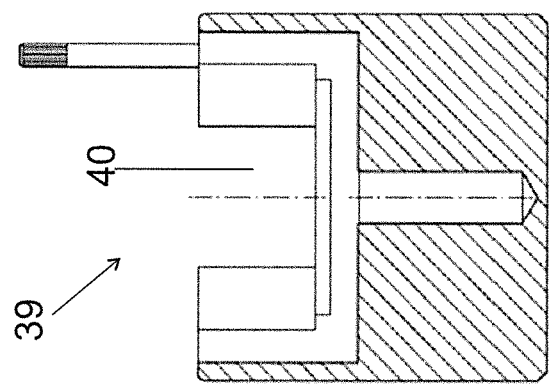
Fig. 10
Fig. 9
Fig. 8

DEVICE AND METHOD FOR TREATING A FILTRATION MEDIUM

BACKGROUND

1. Field of the Invention

The invention relates to a device for treating a porous filtration medium having a receiving unit consisting of a receiving part and a base part, wherein the porous filtration medium can be received and lifted by the receiving part from a lower part of a filtration device, and the receiving part with the porous filtration medium can be mounted on the base part, and wherein the receiving part is formed so as to be latchable to the base part.

2. Description of the Related Art

The invention further relates to a method for treating a porous filtration medium with a receiving unit of a device, said receiving unit consisting of a receiving part and a base part
- in which the receiving part is placed on the filtration medium that is arranged in a lower part of a filtration device and exposed to a liquid sample, wherein a fixing edge arranged in the receiving part is connected to an edge of the filtration medium,
- in which the receiving part with the connected filtration medium is lifted from the lower part and placed on the base part, whereby the receiving part and the base part are latched together.

Primarily microbiological methods, which detect individual microorganisms by using cultivation steps, are currently used for routine investigations. These methods are, however, very time-consuming and may take several days to detect contamination of the aqueous medium. Modern, rapid methods for detecting microorganisms, such as real-time PCR, antibody assays or analytical microarrays, facilitate the quick detection of microbial contamination. But first, in order to lower the detection limits in these detection methods and ideally also to be able to detect a single microbe, fast, effective enrichment steps are required in order to concentrate a large sample volume of up to several liters into a few hundred microliters. The concentrated sample allows for better handling with less consumption of reagents and can be processed according to any of the subsequent detection methods.

Various treatment methods using porous media such as filters and membranes have become established in the analysis of liquids and gases. For instance, a filtration method for enriching and concentrating dissolved or particulate substances has been established. Such concentration is generally necessary if the concentrations of the contaminants are too low to perform direct evaluations. Filtration methods are the precursor of further analytical methods, such as visual evaluations, as well as of further physical and chemical reactions for signal amplification.

Only small sample volumes can be used for newer, more sensitive analytical methods, e.g. polymerase chain reaction (PCR), and the preparation of the samples used in such methods. Filtration membranes with diameters of 47 mm or 25 mm are typically used to filter for concentration purposes the sample volumes of more than 100 ml that are typical in many cases. Even after filtration, when the substances or particles are present in concentrated form on the filtration membrane, the membrane-bound particles cannot be conveyed directly to analysis because of the size of the membrane. It is necessary to transfer the retained substances to a sample volume, which ideally should not exceed 1 ml, in order to create a sample preparation for the subsequent analysis in standard reaction vessels that will fit into tabletop centrifuges, which are typically part of the standard equipment available in any laboratory.

A device and a method for treating a porous filtration medium with a receiving unit consisting of a receiving part and a base part are known from WO 2011/057707 A2. With the receiving part the porous filtration medium can be lifted off from a lower part of a filtration device, and the receiving part with the porous filtration medium can be placed on the base part, the receiving part and the base part being designed so as to be reversibly connected to each other. The known device, which has basically proved itself in practice, serves to transfer filtered substances by means of back-flushing from a filter (filtration medium) to a receiving vessel connected to the receiving part.

A disadvantage of this device is that, because of the distribution of pore sizes in most membrane filters, numerous particles are separated out not on the surface of the membrane filter but rather in deeper layers so that a quantitatively complete back-flushing of the particles is not possible. Non-specific adsorption events of the retained particles on the membrane also intensify this problem.

A culture-medium unit and a method for receiving a filter from a filtration device are known from DE 10 2008 005 968 A1. This culture-medium unit consists of a cover or receiving part, which forms the actual transfer unit, and a lower part filled with a culture medium. The upper part, which is designed to serve as a receiving part, has a fixing edge which can be connected to an edge of the filter by means of an adhesive bond in order to remove the filtration medium from the filtration device or treatment device.

Also known from DE 10 2008 005 968 A1 is a method for the microbiological examination of liquid samples, in which a cover or receiving part of a culture-medium unit is placed on a filter, designed as a membrane filter and having a fixing edge, which is arranged in a lower part of a filter device or treatment device. In this case the fixing edge of the receiving part is connected to an edge of the filter by means of an adhesive layer. The receiving part with the filter is then lifted from a filter support in the lower part of the filter device and placed on the surface of a nutrient medium arranged in the lower part of a culture-medium unit, and the cover or the receiving part covers the dish-shaped lower part.

However, a disadvantage of the known filtration units and the corresponding methods, which have proved their usefulness for classic, microbiological membrane applications in which only particles are removed or in which established colonies are visually evaluated in the field of microbiology, is the fact that after filtration the retained particles or their constituent substances can no longer be removed from the membrane by flushing in such a manner that highly concentrated suspensions result.

The dissolving of a porous filtration medium with the goal of performing a PCR analysis of the constituent substances is known from JP 2012-019723 A, from L. J. DiMichele (Am. Soc. Brew. Chem., 1993, Vol. 51, No. 2, pp. 63-66), from K. Nakamura (Journal of Aerosol Research, 2003, Vol. 18, No. 3, pp. 177-180), and from K. Stark (Applied and Environmental Microbiology, 1998, Vol. 64, No. 2, pp. 543-548).

However, a disadvantage of the method described in each of these documents is the high risk of contamination since the filtration medium must be picked up, folded and transferred to a reaction vessel (generally a 1.5- to 2-ml vessel) using tweezers. The subsequent addition of a solvent for the membrane also represents a risk of contamination in an open system.

Also known from JP 2012-019723 A is the method of using acetone to dissolve cellulose membranes on which microorganisms are fixed and adding aqueous buffering solutions in order to derive a solution containing the microorganisms.

A disadvantage of this method is that this process again precipitates out some cellulose in fiber form and that the cellulose fibers have the undesired effect of binding to portions of the microorganisms or the DNA, thus making the quantitative analysis of the microorganisms more difficult. Certain additives, e.g. cetyltrimethylammonium bromide, are added to reduce the undesirable adsorption of the microorganisms or DNA on the fibers. But a complete quantitative analysis cannot be achieved.

Further, a method is known from L. J. DiMichele (Am. Soc. Brew. Chem., 1993, Vol. 51, No. 2, pp. 63-66) for dissolving polycarbonate membranes, on which microorganisms are fixed, in a mixture of water and chloroform (200 μl water and 300 μl chloroform) with the goal of enriching the microorganisms in the aqueous phase. After the aqueous phase is transferred to a new vessel, the microorganisms are pelletized by means of centrifugation. A washing step follows and then the PCR.

A disadvantage of this method is that microorganisms do not in practice accumulate in the upper aqueous phase. Rather, the microorganisms tend to sediment in the organic phase (lower phase) or in the boundary layer so that the complete recovery of the microorganisms cannot be achieved with this method. Furthermore, the described method does not have a lysis step to disrupt the microorganisms so that it must be assumed that numerous intact cells are used for the PCR and thus amplification will not be possible for a large portion of the DNA.

Further, a method is known from K. Stark (Applied and Environmental Microbiology, 1998, Vol. 64, No. 2, pp. 543-548) for dissolving in chloroform polyethersulfone membranes on which microorganisms are fixed. TE buffers are then added and there follows a ten-minute extraction of DNA into the aqueous phase under agitation at room temperature. The aqueous solution is then subjected to DNA precipitation with alcohol before the PCR evaluation is performed.

A disadvantage of this method is that only a small proportion of the DNA can be extracted into the aqueous phase because there is no prior lysis step to disrupt the microorganisms and thereby make the DNA freely accessible. Rather, using this method results in the sedimentation of the still intact microorganisms into the lower organic phase or into the boundary layer between the organic and aqueous phases.

A method is also known from K. Sen (Applied and Environmental Microbiology, 2007, Vol. 73, No. 22, pp. 7380-7387) for folding the filtration medium with a pair of tweezers and transferring it into a reaction vessel. The membrane does not undergo a dissolving step but rather is only rinsed with, for instance, a commercial lysis buffer, or the membrane is mechanically stressed by vortexing it together with grinding balls, which serves to disrupt the cells. K. Sen uses various commercial kits for DNA isolation.

A disadvantage of the methods described is not only the increased risk of contamination from folding and transferring the membrane with tweezers, but also that it is not possible to completely rinse the microorganisms from the membrane because microorganisms are frequently also separated out in deeper layers of the membrane, and also that non-specific adsorption may occur on the membrane so that a superficial flushing step is not effective. Another complicating factor is that with a membrane that has been folded up small in a reaction vessel, no targeted back-flushing of the membrane is possible, instead only undirected mixing or vortexing of the membrane and flushing solution can be accomplished.

From WO 2012/031156 A1 a filtration device is known which enables work to be carried out in a contamination-free setting by retaining the filtration medium (diameter of filtration surface: 13 mm) in the sealable device and disrupting the cells directly on the membrane using grinding balls and vortexing. The free DNA passes through the membrane in a subsequent filtration step.

A disadvantage of this method is that the quantitatively complete disruption of the cells is not possible because a large portion of the microorganisms generally penetrates into the deeper layers of the membrane and is thereby shielded from the grinding balls. This buffering effect also has a negative influence on the degree of disruption of the microorganisms because a large proportion of the impacts are absorbed by the membrane. In addition, the subsequent step of filtering the DNA through the membrane will be incomplete because DNA has a tendency to form non-specific bonds, in this case on the membrane. Moreover, the diameter of the filtration surface is limited to 13 mm in this device as a result of its compatibility with common centrifuge models and adapters. However, this small diameter of the filtration medium results in considerably longer filtration times for large sample volumes.

EP 2 402 456 A1 discloses a method for analyzing microorganisms in water samples in which a water sample containing microorganisms is injected by a first syringe into a Minisart® syringe filter with a cellulose-ester membrane to retain the microorganisms. After the syringe is removed, one end of the syringe filter is connected to a receiving vessel, while the other end of the syringe filter is connected to a second syringe filled with a polar aprotic solvent such as DMSO (dimethyl sulfoxide). DMSO is injected into the syringe filter until the pressure point is reached in order to dissolve the membrane with the retained microorganisms and collect the solution in the receiving vessel. Centrifugation of the solution in the receiving vessel is followed by cell lysis and further microbiological analytical steps, such as PCR.

Disadvantages of the method known from EP 2 402 465 A1 are the successive handling with two different syringes—one of which contains a water sample and the other of which contains the solvent for the cellulose-ester membrane—and the fact that when injecting the DMSO into the syringe filter the injection pressure must not be too high, i.e. it must be less than the pressure point, so that the syringe filter is not damaged.

The task of the present invention is, therefore, to provide a device and a method with which it is possible to transfer a porous filtration medium including retained microorganisms easily, safely and without risk of contamination to a receiving vessel in order to make the sample quantitatively completely accessible for DNA extraction and molecular biological analysis.

SUMMARY OF THE INVENTION

The task relating to the device is solved in that, on the side facing the filtration medium, the base part has an incubation chamber which is connected to a base part outlet that is facing away from the receiving part, and in that the outlet has a projection onto which a receiving vessel containing a solvent for dissolving the porous filtration medium can be detachably push-fitted.

Through the placement of the incubation chamber in the base part and the connection via the outlet to the receiving vessel with the solvent, it is possible to transfer the porous filtration medium including retained microorganisms easily, safely and without risk of contamination to the collection vessel in order to make the sample quantitatively completely accessible for DNA extraction and molecular biological analysis.

According to a preferred embodiment of the invention, the incubation chamber in the base part is conical towards the outlet.

This conical shape guarantees that despite the centrifugation angle of a fixed-rotor centrifuge no dead volume is created in the incubation chamber of the receiving unit, which could lead to residual fluid build-up. Without this conical shape, and depending on the centrifuge model, residual fluid would remain laterally in the base part of the receiving unit as a result of centrifugal force.

According to a further preferred embodiment of the invention, the solvent used to dissolve the filtration medium is an organic solvent, preferably chloroform or methylene chloride.

According to a preferred embodiment of the invention, the receiving vessel to be push-fitted to the base part contains not only the solvent but also the grinding balls that facilitate cell disruption.

According to a preferred embodiment of the invention, the receiving vessel to be push-fitted to the base part contains the solvent as well as a lysis buffer that facilitates cell disruption. The lysis buffer is preferably an aqueous fluid that will not emulsify with the solvent but rather will form a two-phase system with the solvent.

According to a further preferred embodiment of the invention, the receiving vessel that is push-fitted on the base part contains not only the solvent but also a lysis buffer that facilitates cell disruption, and grinding balls.

The open end of the receiving vessel can be sealed with a cover to prevent fluids from leaking. For this purpose, the receiving vessel has, for instance, at its open end an outside thread by means of which the cover can be screwed on.

According to a further preferred embodiment of the invention, the outlet of the base part has an outlet channel designed as an oblong slot arranged at a right angle to the longitudinal axis of the base part, and having a narrow clear width which is smaller than the outside diameter of the grinding balls. This ensures that the grinding balls will not penetrate into the incubation chamber and will remain in the receiving vessel.

According to a further preferred embodiment of the invention, an inner wall of the receiving part can be positioned outside a surface of the filtration medium that can be used for filtration, and a fixing edge arranged in the receiving part can be positioned on the edge of the filtration medium, and the fixing edge of the receiving part can be attached to the edge of the filtration medium by means of an adhesive bond. In an alternative embodiment of the invention, a fixing edge of the receiving part can be attached to a corresponding ring-shaped clamping part at the edge of the filtration medium by means of a mechanical clamping connection. This allows the receiving part to be easily attached to the filtration medium, and the receiving part and filtration medium can easily be placed on the base part without risk of contamination. A filtration medium made of polycarbonate or polyethersulfone is preferred.

According to a further preferred embodiment of the invention, the receiving unit can be attached to the receiving vessel arranged vertically at the bottom in a centrifuge adapter and can be centrifuged with the centrifuge adapter in a centrifuge, whereby the filtration medium dissolved in the solvent, including retained microorganisms, can be completely transferred into the receiving vessel.

The task related to the method is solved in that a receiving vessel containing a solvent for dissolving the porous filtration medium is detachably connected to an outlet arranged on the base part, and that the receiving unit with the receiving vessel is inverted and shaken, whereby the solvent is added to the filtration medium by way of the outlet of the base part and dissolves the filtration medium.

The filtration medium, with the receiving part of the receiving unit, can easily be detached from a lower part of a filtration device and placed on the base part. Once a cover is removed from the receiving vessel with the solvent, the receiving vessel can easily and without risk of contamination be push-fitted onto an outlet on the base part. By inverting and gently shaking the receiving unit, the solvent is introduced into the incubation chamber, and the filtration medium is dissolved within a few seconds and then transferred to the receiving vessel. Although the pressure in the incubation chamber of the receiving unit is increased as a result of the partly vaporizing organic solvent, the receiving part and the base part remain connected because they are latched together.

The dissolved filtration medium with the retained particles provides a good starting point for further sample preparation, e.g. a DNA extraction, and for various analytical methods, such as PCR.

According to a preferred embodiment of the invention, grinding balls, which promote cell disruption, are added to the receiving vessel together with the solvent.

According to a further preferred embodiment of the invention, the receiving unit is attached to the receiving vessel arranged vertically at the bottom in a centrifuge adapter and centrifuged in a centrifuge, whereby the filtration medium dissolved in the solvent, including retained microorganisms, is completely transferred into the receiving vessel. The receiving vessel is then removed from the receiving unit and sealed with a cover.

According to a further preferred embodiment of the invention, the receiving vessel is removed from the receiving unit and sealed with a cover, and a lysis buffer to promote cell disruption is added to the receiving vessel before it is sealed with the cover.

The lysis buffer can be used as an alternative to or in addition to the use of grinding balls. The lysis buffer is preferably an aqueous fluid that will not emulsify with the solvent but rather will form two separate phases (solvent and lysis buffer).

An example of an appropriate lysis buffer for the method according to the invention is the product "Cell Lysis Solution" (item no. 2900024) from 5 PRIME. The sealed receiving vessel is then incubated under agitation. If both a lysis buffer and grinding balls are used to bring about cell disruption, incubation to promote disruption is performed in a homogenizer. If only a lysis buffer is used, tris-EDTA buffer with 0.01% sodium dodecyl sulfate (see Example 1, Step 9) need not be added because the lysis buffer itself leads to the formation of two phases and the DNA of the lysed microorganisms is enriched in the aqueous lysis-buffer phase.

According to a further preferred embodiment of the invention, the sealed receiving vessel is processed in an agitation incubator or homogenizer, with cell disruption of the microorganisms being facilitated by using grinding balls and/or the lysis buffer.

The device for treating the filtration medium can be shipped in sterile packaging.

Further features of the invention can be obtained from the following detailed description and from the attached drawings, in which examples of preferred embodiments of the invention are depicted.

BRIEF DESCRIPTION OF THE DRAWINGS

FIG. 8 is a side view in cross-section of the centrifuge adapter of FIG. 10 along the line VIII-VIII.

FIG. 9 is a side view of the centrifuge adapter of FIG. 10 viewed from direction IX.

FIG. 10 is a top view of the centrifuge adapter of FIGS. 8 and 9.

DETAILED DESCRIPTION

Figure 1:
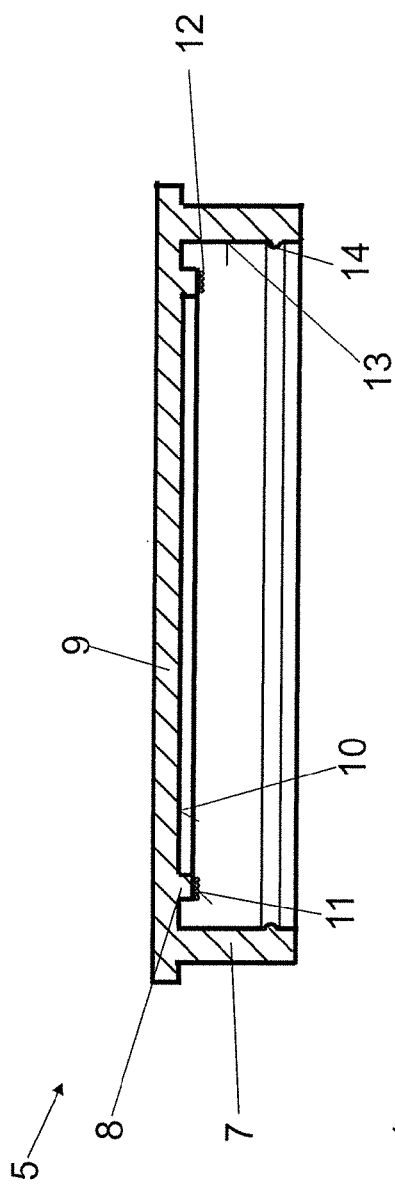
FIG. 1 is a side view in cross-section of a receiving part of a device for treating a porous filtration medium.
Figure 2:
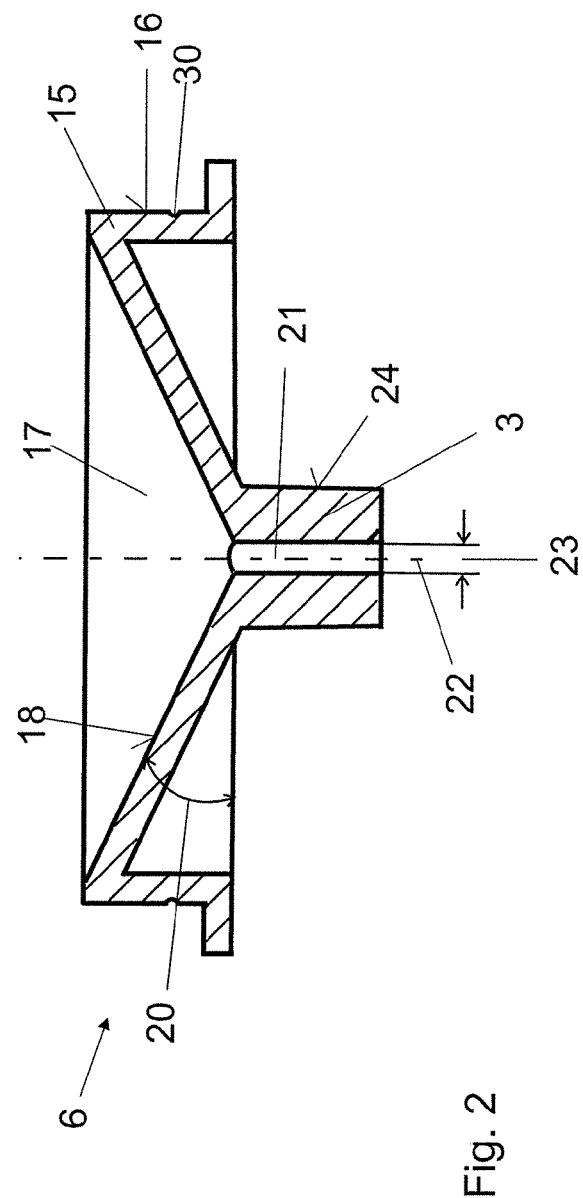
FIG. 2 is a side view in cross-section of a base part of a device for treating a porous filtration medium.
Figure 3:
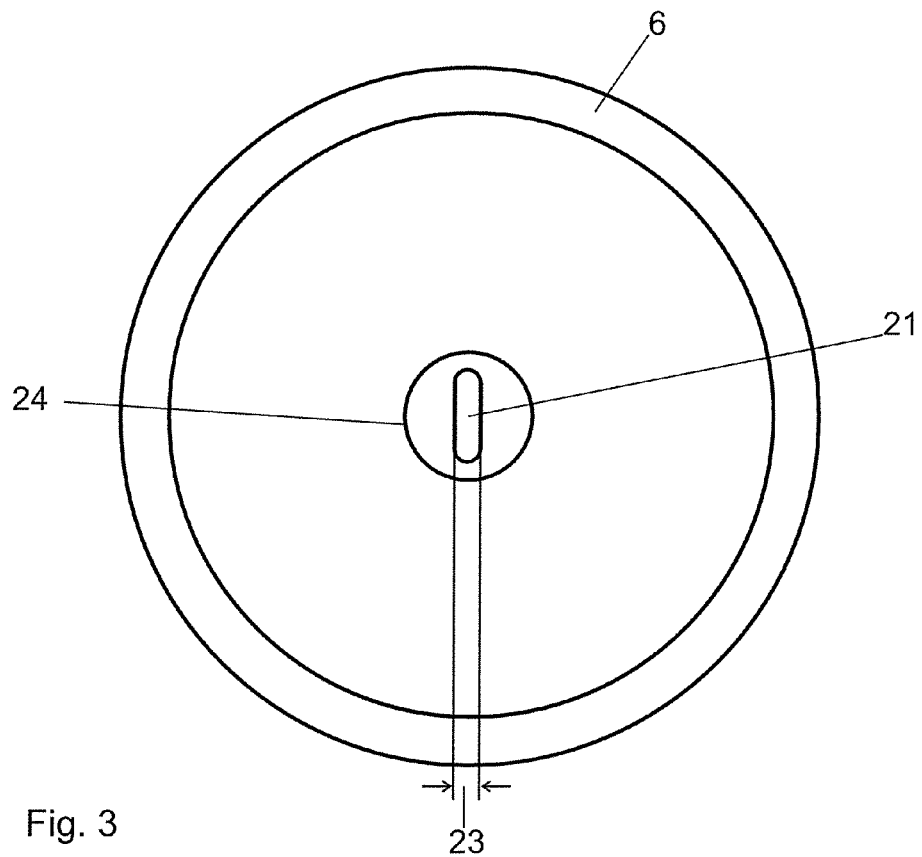
FIG. 3 is a view from below of the base part of FIG. 2.

A device 1 consists essentially of a receiving unit 2 with an outlet 3 and a receiving vessel 4.

The receiving unit 2 comprises two parts and consists of a receiving part 5 and a base part 6.

The receiving part 5 forms a circumferential contour with an outer wall 7 and an inner wall running parallel to it. The receiving part 5 is sealed in a vertical direction at the top by a top wall 9. On its inner surface 10 of the receiving part, facing the base part 6, the top wall 9 has the inner wall 8, the free end face of which forms a fixing edge 11. In the exemplary embodiments the fixing edge 11 has an adhesive layer 12 made of an appropriate adhesive.

The adhesive layer 12 could, for example, be made of a PSA dispersion adhesive or of acrylate-copolymer microspheres. Appropriate adhesives are those that are based on organic solvent(s) and that are soluble in organic solvents that are used in the context of dissolving a filtration medium. Furthermore, the adhesives must demonstrate permanent adhesive strength (from the date of production of the device until it is used by the user). The adhesive must be sterilizable using ETO (ethylene oxide). In addition, adhesives that demonstrate no non-specific reactions or signals with reagents and reaction methods used in subsequent analyses are used. In particular it is preferred that the adhesive be free of DNA and that it contain no substances which might interfere with the subsequent analyses through coloration, fluorescence or chemical reaction.

The outer wall 7 has an inside outer wall surface 13 with a ridge 14 running around its circumference.

The base part 6 has a circumferential outer wall 15 with an outer surface 16 that corresponds with, i.e. interacts with, the inner wall 13 of the receiving part 5. On the side facing the receiving part 5, the base part 6 has a funnel-shaped incubation chamber 17 with a conical drainage surface 18 that is inclined to the horizontal at an angle 20 of, for example, 25° sloping down to the outlet 3. The outlet 3 has an outlet channel 21 designed as an oblong slot with a narrow clear width arranged at a right angle to the longitudinal axis 22 of the base part 6.

The exterior lateral surface of the outlet 3 forms a slightly conical projection 24 onto which the receiving vessel 4 can be detachably push-fitted. At its open end 26, the receiving vessel 4 has an outside thread 27 and can be tightly sealed by screwing on a cover (not shown) having an inside thread. The receiving vessel 4 contains a solvent 28 and grinding balls 29.

Alternatively, instead of or in addition to the grinding balls 29, the receiving vessel 4 can contain a lysis buffer for the microorganisms retained by a filtration medium 37, wherein the lysis buffer, as an aqueous liquid, forms a two-phase system with the solvent 28.

Figure 4:
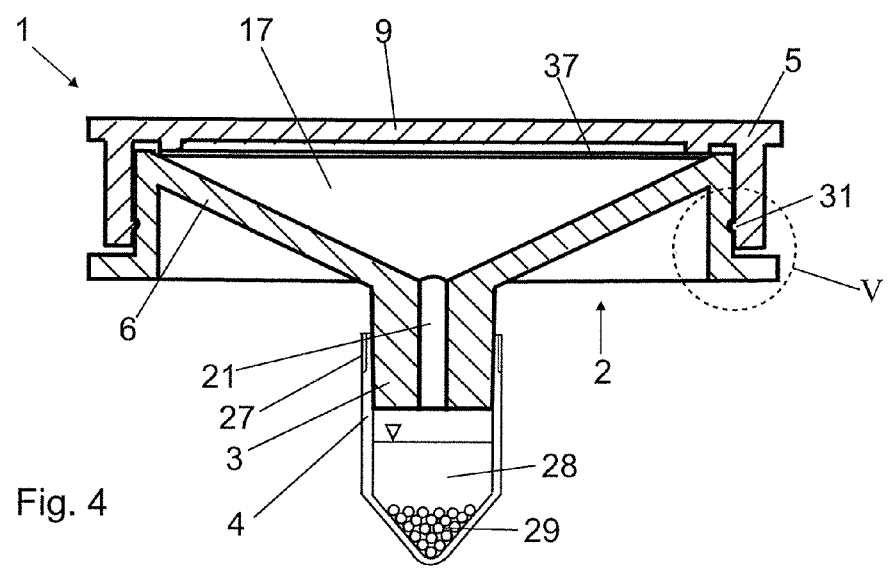
FIG. 4 is a side view in cross-section of a receiving unit with received porous filtration medium, the receiving part and base part of said unit being latched together, and with a push-fitted receiving container containing solvent and grinding balls.
Figure 5:
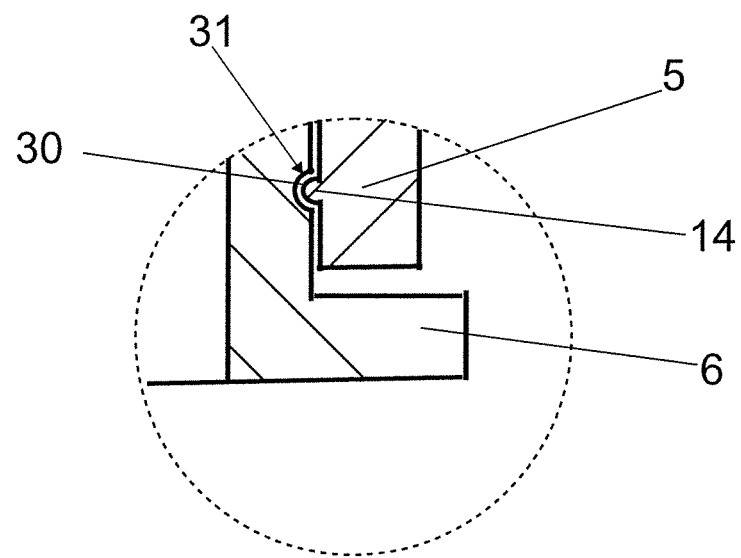
FIG. 5 is an enlarged view of detail V (latching arrangement) of FIG. 4.
Figure 6:
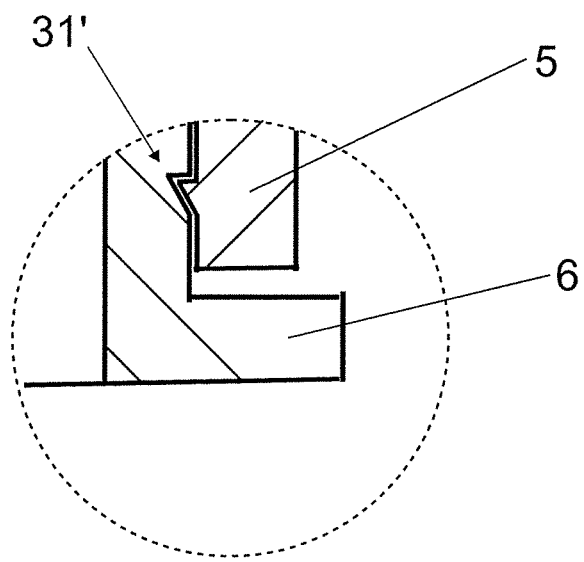
FIG. 6 is an enlarged view of a further latching arrangement corresponding to detail V of FIG. 4.
Figure 7:
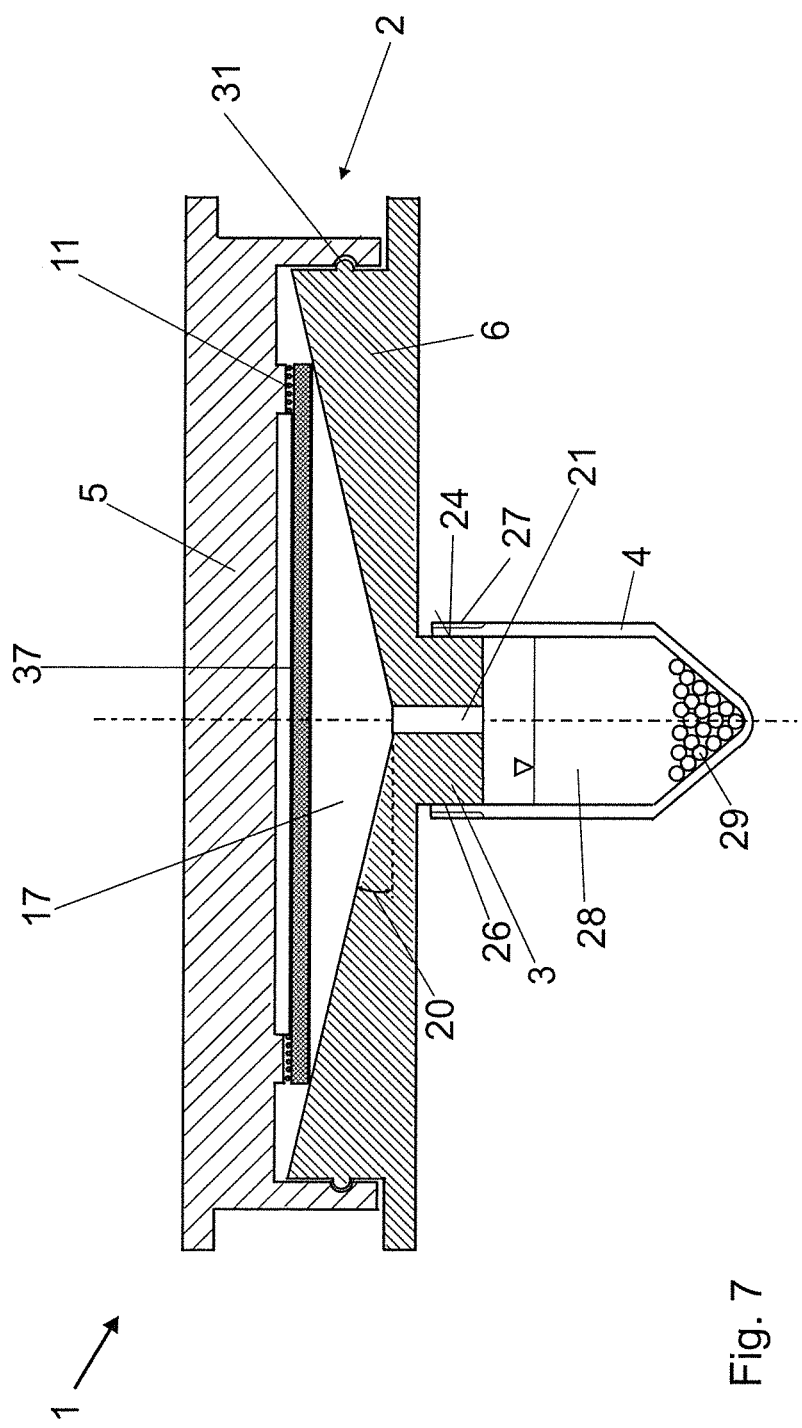
FIG. 7 is a side view in cross-section of a further receiving unit with received a porous filtration medium, the receiving part and base part of said unit being latched together, and with a push-fitted receiving container containing solvent and grinding balls.

The base part 6 has a ring-shaped indentation 30 running around its outer surface 16 that corresponds to the ridge 14 on the receiving part 5 and forms a latching arrangement 31 (see FIGS. 4, 5, 7). The latching arrangement 31 may also be designed to be irreversible, as depicted in FIG. 6.

Figure 11:
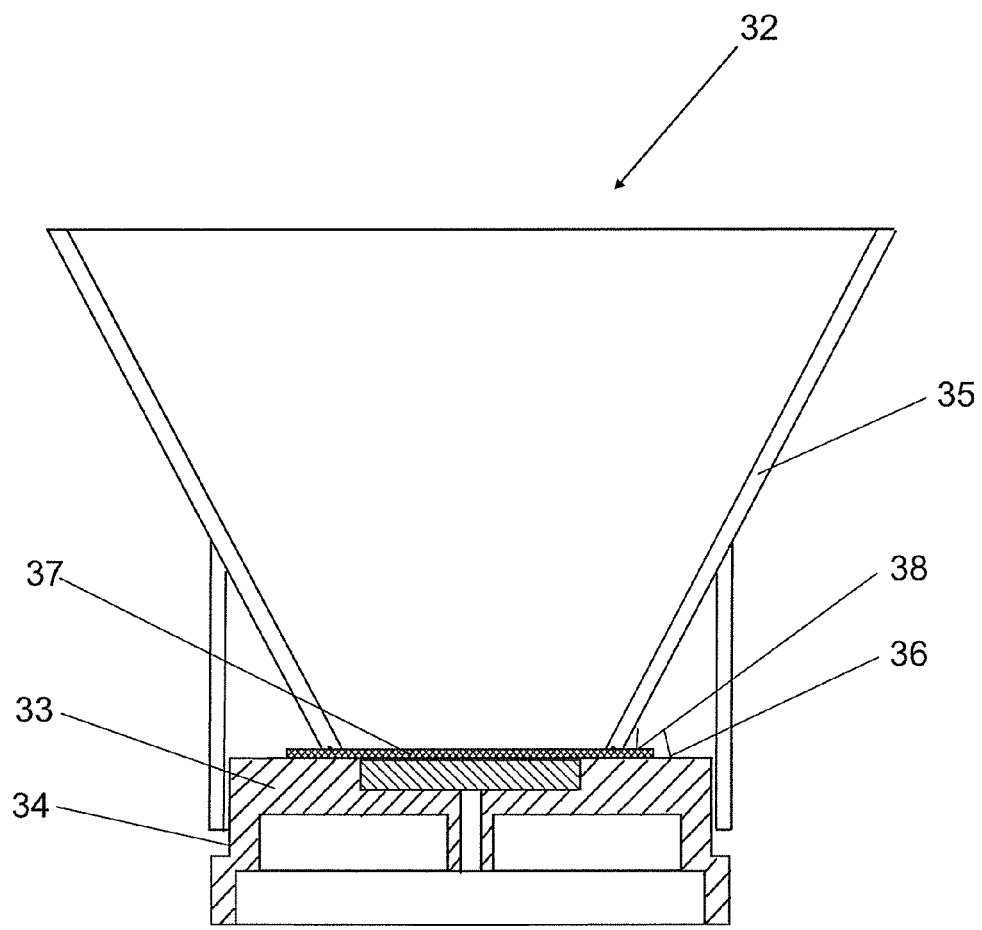
FIG. 11 is a side view in cross-section of a filtration device according to the prior art with a filtration medium arranged on a lower part.

A known filtration device 32 according to FIG. 11 consists of a lower part 33 with a receiving shoulder 34, on which a funnel-shaped attachment 35 can be mounted. The preferably disc-shaped filtration medium 37, which is designed, for instance, as a porous filter membrane, is arranged between the attachment 35 and a filter-supporting surface 36 of the lower part 33.

After a filtering process, the attachment 35 can be removed from the lower part 33 and the receiving part 5 of the device 1 can be placed on the lower part 33 in place of the attachment 35. In the process, the receiving part 5 with its fixing edge 11 is placed on an edge 38 of the disc-shaped filtration medium 37 so that the disc-shaped filtration medium 37 adheres to the adhesive layer 12 of the fixing edge 11 and can be lifted off the lower part 33.

The device 1 with the receiving vessel 4 can be placed in a centrifuge adapter 39, which has an appropriately adapted recess 40.

Treatment of the porous filtration medium 37 with the receiving unit 2, which consists of the receiving part 5 and the base part 6, of the device 1 is carried out according to the following steps:

the receiving part 5 is placed on the filtration medium 37, which is arranged in the lower part 33 of the filtration device 32 and is exposed to a liquid sample, with a fixing edge 11 arranged in the receiving part 5 being connected with an edge 38 of the filtration medium 37, the receiving part 5 with the attached filtration medium 37 is lifted off the lower part 33 and placed on the base part 6, whereby the receiving part 5 and the base part 6 are latched together by means of the latching arrangement 31, 31', a receiving vessel 4 containing a solvent 28 for dissolving the porous filtration medium 37 and grinding balls 29 is detachably connected to the outlet 3 arranged on the base part 6, the receiving unit 2 with the receiving vessel 4 is inverted and gently shaken, whereby the solvent 28 is added to the filtration medium 37 via the outlet 3 of the base part 6, and dissolves the filtration medium 37.

The following steps can then be carried out:

the receiving unit 2, with the receiving vessel 4 arranged vertically at the bottom, is mounted in a centrifuge adapter 39 and centrifuged in a centrifuge, whereby the filtration medium 37 dissolved in the solvent 28, including retained microorganisms, is completely transferred into the receiving vessel 4, the receiving vessel 4 is removed from the receiving unit 2 and sealed by screwing on a cover, the sealed receiving vessel 4 is processed in a homogenizer, and the cell disruption of the microorganisms is facilitated by the grinding balls 29.

If a lysis buffer is used instead of or in addition to the grinding balls 29 for cell disruption, the following steps can be carried out:

the receiving unit 2, with the receiving vessel 4 arranged vertically at the bottom, is mounted in a centrifuge adapter 39 and centrifuged in a centrifuge, whereby the filtration medium 37 dissolved in the solvent 28, including retained microorganisms, is completely transferred into the receiving vessel 4, the receiving vessel 4 is removed from the receiving unit 2 and is filled with lysis buffer before being sealed with a screw-on a cover, the sealed receiving vessel 4 is processed in a homogenizer, and the cell disruption of the microorganisms is facilitated by the grinding balls 29 and/or lysis buffer.

If cell disruption is carried out without using grinding balls and only with a lysis buffer, cell disruption can alternatively also take place in an agitation incubator instead of in a homogenizer.

The following experiments were performed:

Example 1

Determination of Sensitivity for Detecting *Bacillus subtilis* Using the Device 1 Including the Receiving Vessel 4.

A dilution series of an exponential phase culture of *Bacillus subtilis* in a 0.9% NaCl solution was incubated, using double determination after filtration, on Sartorius nutrient agar (47-mm cellulose-nitrate membrane with a pore diameter of 0.45 µm; enumeration of the colonies after 24 h), and at the same time one sample per dilution stage was processed according to a preferred embodiment of the invention.

A preferred embodiment of the invention comprises the following process steps:

1. Membrane filtration of an aqueous sample (membrane diameter 47 mm, track-etched polycarbonate membrane, pore diameter 0.4 µm, membrane thickness 6 to 11 µm) using a lower part 33 (ideally made of plastic; ETO sterile) as depicted in FIG. 11.
2. Removal of the attachment 35 and lifting up of the membrane filter/filtration medium 37 with the help of the adhesive bond on the fixing edge 11 of the receiving part 5 (made of polypropylene; ETO sterile).
3. Connecting of the receiving part 5 and base part 6 of the receiving unit 2 by means of the latching arrangement 31.
4. The receiving vessel 4 (made of polypropylene; ETO sterile) with attached screw-on cover with a capacity of 2 ml contains 15 steel balls/grinding balls 29 (diameter 3 mm) and 750 µl chloroform (molecular biology grade; above all free of DNA and DNase). After the receiving vessel 4 is opened, it should be attached to the outlet 3 of the base part 6 by means of a plug-in connection (downward tapering projection 24 is inserted into the open end 26 of the receiving vessel 4).
5. The receiving unit 2 with receiving vessel 4 is inverted and gently shaken to transfer the chloroform completely from the receiving vessel 4 to the receiving unit 2. The receiving unit 2 with the receiving vessel 4 is then inverted and gently swirled for several seconds to ensure that the membrane filter/filtration medium 37 dissolves completely.
6. The receiving unit 2 with attached receiving vessel 4 is turned upright (receiving part 5 faces upwards, receiving vessel 4 faces downward) and placed in the special centrifuge adapter 39. The adapter is a swing-out centrifuge adapter to ensure the quantitatively complete transfer of the dissolved membrane/filter medium 37, including the particles retained by the membrane 37, and of the solvent 28. Furthermore, the centrifuge adapter 39 is constructed such that the receiving vessel 4 cannot become loose or fall off during the centrifugation step. The centrifuge adapter 39 is mounted on a suitable centrifuge and centrifuged for one minute at at least 3,000×g in order to completely transfer the membrane 37 dissolved in the chloroform, including retained microorganisms, to the receiving vessel 4 with the steel grinding balls 29.
7. The receiving vessel 4 is removed from the receiving unit 2 and tightly sealed by screwing on the attached cover.
8. To disrupt the microorganisms and make their DNA accessible, the receiving vessel 4 is processed for 2 min at 6.5 m/s in a homogenizer (FastPrep-24 Instrument from MP Biomedicals). (Alternatively, other comparably performing homogenizers can be used.)
9. The receiving vessel 4 is removed from the homogenizer, and 500 µl of 1×TE buffer (tris-EDTA) with 0.01% SDS (sodium dodecyl sulfate) are added (molecular biology grade).
10. A 10-minute extraction (extraction of DNA from the organic to the aqueous phase) at room temperature follows. To do this, the receiving vessel 4 is attached either horizontally on a vortexer or horizontally on a thermomixer at 750 RPM.
11. Add a spatula tip of DNA- and DNase-free silicone paste (e.g. Phase Lock Gel from 5 PRIME or GE Bayer Silicones, high viscosity) through the opening in the receiving vessel 4.
12. Centrifuge the receiving vessel 4 for 3 min at 16,000×g.
13. Because of the different densities, three phases separated: The top, aqueous phase including DNA, the middle, silicone-gel phase as a barrier layer, and the bottom, organic phase. The entire top, aqueous phase is transferred to a new, empty receiving vessel 4 using a pipette (a 1.5-ml reaction vessel is sufficient).
14. Add 600 µl isopropanol (molecular biology grade) and 2 µl glycogen as a DNA carrier (molecular biology grade) and invert the reaction vessel 4 50 times.
15. Centrifuge the reaction vessel 4 for 3 min at 16,000×g, so that a small, white DNA-glycogen pellet forms on the floor of the reaction vessel 4.

16. Discard the isopropanol; the DNA-glycogen pellet remains in the reaction vessel 4.
17. Use a pipette to add 600 µl of 70% ethanol to the DNA-glycogen pellet and invert the reaction vessel 4 20 times.
18. Centrifuge the reaction vessel 4 for 1 min at 16,000×g.
19. Discard the 70% ethanol (remove with a pipette); the DNA-glycogen pellet remains in the reaction vessel 4.
20. Dry the DNA-glycogen pellet in the opened reaction vessel 25 either for 10 min at 37° C. in a sealed thermoblock or for 15 to 20 min under the sterile bench.
21. Dissolve the pellet in 50 to 100 µl of rehydration buffer (10 mM tris, 1 mM EDTA, pH 7-8, free of DNA and DNase) for 1 h at 65° C. in a thermoblock (in the closed reaction vessel).
22. Analysis/detection with quantitative real-time PCR, e.g. with universal or specific bacterial primers.

Reaction Conditions, Example 1:
25 µl PCR reaction volume (12.5 µl MAXIMA SYBR Green qPCR Master Mix from Fermentas, 10 nM ROX,
0.3 µM Forward Primer SEQ ID NO. 1: 5"-AAGTC-GAGCGGACAGATGG-3",
0.3 µM Reverse Primer SEQ ID NO. 2: 5"-TGCGGT-TCAAACAACCATCCG-3",
10 µl DNA (obtained according to the preferred embodiment of the invention),
add water (PCR grade) for a total of 25 µl.
Temperature profile: 10 min at 95° C.; 40 cycles of 15 seconds at 95° C., 30 seconds at 60° C., 30 seconds at 72° C. (fluorescence detection at 72° C.); melting curve with 1 min at 95° C., 30 seconds at 55° C., temperature ramp up to 95° C. with fluorescence measurement, 30 seconds at 95° C.
Results of Exemplary Embodiment 1:

TABLE 1

Ct (cycle threshold) values and melting points of Exemplary Embodiment 1

| Sample designation | Cycle Threshold | Melting point of the amplicon [° C.] |
|---|---|---|
| 2 × 10² CFU/ml* | 34.22 | 83.80 |
| 2 × 10² CFU/ml* | 34.37 | 83.80 |
| 2 × 10³ CFU/ml* | 33.48 | 83.80 |
| 2 × 10³ CFU/ml* | 33.90 | 83.80 |
| 2 × 10⁴ CFU/ml* | 32.18 | 83.80 |
| 2 × 10⁴ CFU/ml* | 32.21 | 83.80 |
| 2 × 10⁵ CFU/ml* | 29.05 | 83.80 |
| 2 × 10⁵ CFU/ml* | 28.91 | 83.80 |
| PCR negative control | No Ct | 69.38 |
| PCR negative control | No Ct | 69.38 |
| PCR negative control | No Ct | 69.38 |

*CFU (colony-forming unit) concentrations determined by plating.

Figure 12:
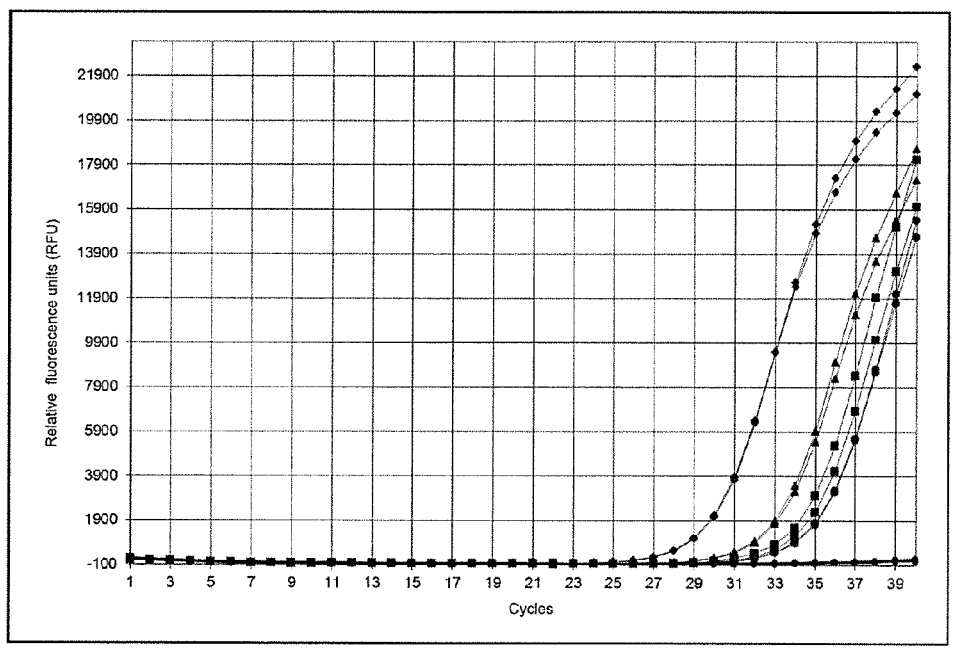
FIG. 12 is curve plots of the samples of *B. subtilis* processed according to a preferred embodiment of the invention.

FIG. 12 shows the curve plots of the samples of *B. subtilis* processed according to the preferred embodiment of the invention: diamonds ($2\times10^5$ CFU/ml), triangles ($2\times10^4$ CFU/ml), squares ($2\times10^3$ CFU/ml), circles ($2\times10^2$ CFU/ml), stars (0 CFU/ml, extraction negative controls). Using the preferred embodiment of the invention, *Bacillus subtilis* can be detected in a sample volume of any size with a sensitivity of at least $2\times10^2$ CFU/ml (using primer with Sequences SEQ 1 and SEQ 2).

Example 2

Invention with a preferred embodiment vs. prior art (L. J. DiMichele, Am. Soc. Brew. Chem., 1993, Vol. 51 No. 2, pp. 63-66, and K. Stärk, Applied and Environmental Microbiology, 1998, Vol. 64, No. 2, pp. 543-548; Further treatment of dissolved filtration medium 37 without a cell lysis step). Sensitivity comparison for the detection of *B. subtilis* spores using device 1 incl. receiving vessel 4 and filtration device 32.

Two membrane filters/filtration medium 37 were processed according to a preferred embodiment of the invention (i.e. cell disruption using grinding balls 29 in a homogenizer). Two membrane filters/filtration medium 37 were processed according to this preferred embodiment of the invention, however without a cell lysis step (corresponds to the prior art according to K. Stark and L. J. DiMichele). Two membrane filters/filtration medium 37 were processed as extraction negative controls according to the preferred embodiment of the invention, however without the application of microorganisms. $10^6$ *B. subtilis* spores were applied to each membrane filter/filtration medium 37, and the two extraction negative controls were brought into contact only with sterile water (PCR grade). The six samples were processed according to the preferred embodiment of the invention as described in Example 1 (Steps 1 to 22). In the case of the prior art samples (according to K. Stark and L. J. DiMichele), receiving vessels 4 without grinding balls 29 were used and the cell-lysis step in the homogenizer was omitted.

Results of Exemplary Embodiment 2:

TABLE 2

Ct (cycle threshold) values and melting points of Exemplary Embodiment 2

| Sample designation | Cycle Threshold | Melting point of the amplicon [° C.] |
|---|---|---|
| PCR negative control | No Ct | 56.92 |
| PCR negative control | No Ct | 56.91 |
| Extraction negative control | No Ct | 56.91 |
| Extraction negative control | No Ct | 56.46 |
| Prior art | 33.23 | 83.97 |
| Prior art | 33.55 | 83.97 |
| Invention (preferred embodiment) | 29.96 | 83.97 |
| Invention (preferred embodiment) | 29.86 | 83.97 |

Figure 13:
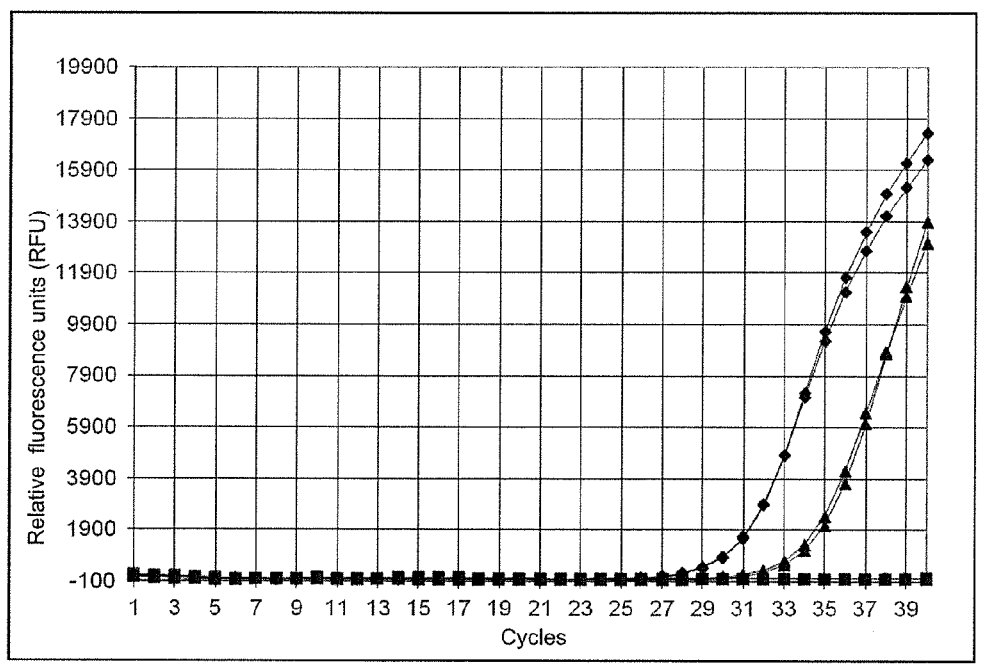
FIG. 13 is curve plots of the spore samples of *B. subtilis* processed according to the preferred embodiment of the invention compared to the prior art.

FIG. 13 shows the curve plots of the spore samples of *B. subtilis* processed according to the preferred embodiment of the invention compared to the prior art: diamonds (preferred embodiment of the invention), triangles (prior art), squares (PCR negative controls and extraction negative controls).

Example 2 demonstrates that the invention in the preferred embodiment is superior to the prior art because an increase in sensitivity of more than 3 Ct units was achieved, which corresponds to a factor of approximately ten genome units/*B. subtilis* spores.

LIST OF REFERENCE NUMBERS

1 device
2 receiving unit
3 outlet of 2
4 receiving vessel
5 receiving part of 2
6 base part of 2
7 outer wall of 5
8 inner wall of 5
9 top wall 10 inner surface of receiving part
11 fixing edge
12 adhesive layer
13 inside surface of outer wall
14 ridge of 5
15 outer wall of 6
16 outer surface of 15
17 incubation chamber
18 drainage surface
20 angle
21 outlet channel
22 longitudinal axis of 6
23 clear width of 21
24 projection of 3
26 open end of 25
27 outside thread of 25
28 solvent
29 grinding balls
30 indentation of 6
31, 31' latching arrangement
32 filtration device
33 lower part of 32
34 receiving shoulder of 33
35 attachment
36 filter supporting surface
37 filtration medium
38 edge of 37
39 centrifuge adapter
40 recess receiving part (5); the second end of the base part (6) defining an outlet (3) facing away from the receiving part (5); the outlet (3) comprises a projection (24) with an outlet channel (21) extending therethrough; and the outlet channel (21) is fluidically connected to the incubation chamber (17); and a receiving vessel (4) detachably push-fit on the projection (24) of the outlet (3), the receiving vessel (4) containing a solvent (28) for dissolving the porous filtration medium (37) and grinding balls (29) that support cell disruption, wherein the outlet channel (21) of the outlet (3) is an oblong slot with a long direction of the oblong slot being aligned at a right angle to a longitudinal axis (22) of the base part (6), and the oblong slot (22) has a clear width (23) transverse to the long direction thereof that is smaller than an outside diameter of the grinding balls (29).

2. The device of claim 1,
wherein
the solvent (28) for dissolving the filtration medium (37) is an organic solvent.

3. The device of claim 2,
wherein
the solvent (28) is chloroform or methylene chloride.

4. The device of claim 1,
wherein
the receiving vessel (4) to be push-fitted to the base part (6) contains both the solvent (28) and a lysis buffer that supports cell disruption.

---

---

The invention claimed is:

1. A device (1) for treating a porous filtration medium (37), the device comprising:
a receiving unit (2) that includes:
a receiving part (5) configured to have the porous filtration medium (37 mounted thereon, and
a base part (6) releasably engaged with the receiving part (5), the base part (6) having opposite first and second ends, the first end facing towards the receiving part (5); and the base part (6) defines conical incubation chamber (17) that widens toward the 5. The device of claim 1, wherein when the receiving vessel (4) is detached from the projection (24) of the outlet (3), an open end (26) of the receiving vessel (4) is configured to be sealed with a cover to prevent fluids from leaking out of the receiving vessel (4).

6. The device of claim 1, further comprising the porous filtration medium mounted on the receiving part (5),
wherein the receiving part (5) has an inner wall (8) positioned outside a surface of the filtration medium (37) that can be used for filtration, and the inner wall (8)

has a fixing edge (11) arranged in the receiving part (5) and positioned on an edge (38) of the filtration medium (37), and at least one of the fixing edge (11) of the receiving part (5) and the edge (38) of the filtration medium (37) has an adhesive thereon forming an adhesive bond between the fixing edge (11) of the receiving part (5) and the edge (38) of the filtration medium (37).

7. The device of claim 1, further comprising the porous filtration medium mounted on the receiving part (5), wherein the filtration medium (37) is made of polycarbonate or polyethersulfone.

8. The device of claim 1, further comprising a centrifuge adapter (39), and wherein the receiving unit (2) is attachable to the receiving vessel (4) arranged vertically at a bottom in the centrifuge adapter (39) so that the receiving unit (2) and the receiving vessel (4) can be centrifuged with the centrifuge adapter (39) in a centrifuge, whereby the filtration medium (37) dissolved in the solvent (28), including retained microorganisms, can be completely transferred into the receiving vessel (4).

\* \* \* \* \*

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Forward
      Primer

<400> SEQUENCE: 1
aagtcgagcg gacagatgg                                                   19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Reverse
      Primer

<400> SEQUENCE: 2
tgcggttcaa acaaccatcc g                                                21
```